United States Patent [19]

Schwulera

[11] Patent Number: 4,904,467
[45] Date of Patent: Feb. 27, 1990

[54] STABILIZED INTERLEUKIN-2

[75] Inventor: Udo Schwulera, Hanau, Fed. Rep. of Germany

[73] Assignee: Biotest Pharma, Frankfurt, Fed. Rep. of Germany

[21] Appl. No.: 65,539

[22] Filed: Jun. 23, 1987

[30] Foreign Application Priority Data

Jun. 28, 1986 [DE] Fed. Rep. of Germany ....... 3621828

[51] Int. Cl.$^4$ ............................................. A61K 37/00
[52] U.S. Cl. .................................. 424/85.2; 424/85.1; 530/351; 514/2; 514/8; 514/12; 514/21; 514/885; 514/970
[58] Field of Search ................. 530/351; 514/2, 8, 12, 514/21, 885, 970; 424/85.2, 85.1

[56] References Cited

U.S. PATENT DOCUMENTS

| | | | |
|---|---|---|---|
| 4,490,289 | 12/1984 | Stern | 530/417 |
| 4,508,833 | 4/1985 | Sonneborn | 530/351 |
| 4,572,798 | 2/1986 | Koths | 530/351 |
| 4,604,377 | 8/1986 | Fernandes et al. | 530/351 |
| 4,645,830 | 2/1987 | Yasushi et al. | 514/21 |
| 4,659,570 | 4/1987 | Terano | 424/85 |
| 4,675,184 | 6/1987 | Hasegawa | 424/85 |
| 4,680,175 | 7/1987 | Estis et al. | 424/85 |
| 4,714,611 | 12/1987 | Yasaburgo et al. | 424/85 |
| 4,789,658 | 12/1988 | Yoshimoto et al. | 514/2 |
| 4,812,557 | 3/1989 | Yasushi et al. | 530/351 |
| 4,816,440 | 3/1989 | Thomson | 514/12 |

FOREIGN PATENT DOCUMENTS 0229016 7/1987 European Pat. Off. .
3307871 10/1986 Fed. Rep. of Germany .

OTHER PUBLICATIONS

Gearing et al., *Lymphokine Research*, vol. 5(1), 1986, pp. 519–520.
Mier et al., *J Immunol*, vol. *128(3), 1982, pp. 1122–1127*.
Mier et al., *Lymphokine*, vol. 6, 1982, pp. 137–163.
Acuto et al., *J. Immunol. Methods* 53, 1982, p. 15–26.
Wang et al, J. Parental Drug Assoc 1980, pp. 452–460.
Sakamoto et al., CA vol. 104, 1986, #205522j.

*Primary Examiner*—Garnette D. Draper
*Attorney, Agent, or Firm*—Sprung Horn Kramer & Woods

[57] ABSTRACT

An interleukin-2 preparation that is extremely pure, stable when stored for a long time, and appropriate for therapeutic purposes, especially in humans, and that also exhibits sufficient activity even after being frozen and thawed several times is obtained by using a special albumin, globulin, or mixture of those substances with sugar alcohols, monomeric or polymeric sugars, gelatins, or other known stabilizers as stabilizers.

4 Claims, 4 Drawing Sheets

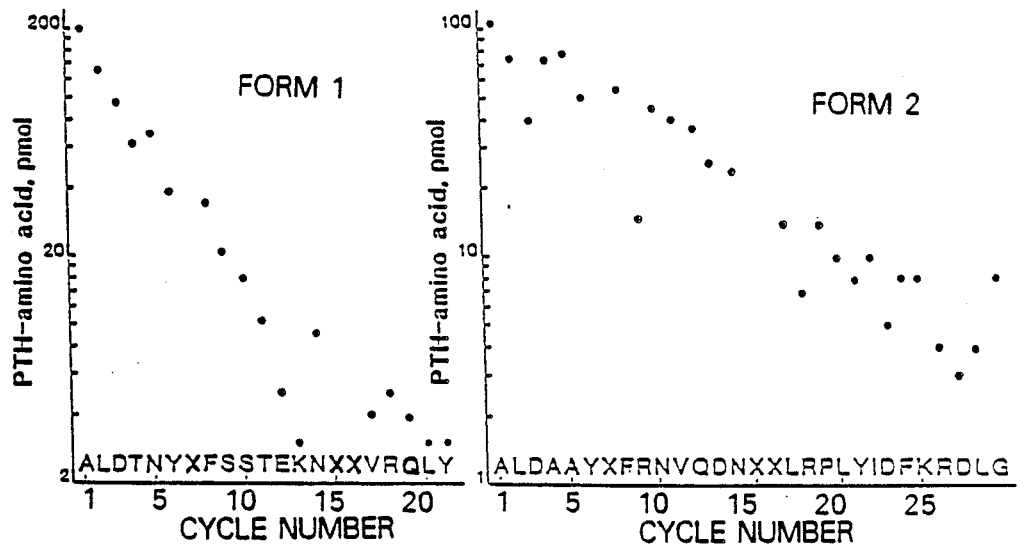
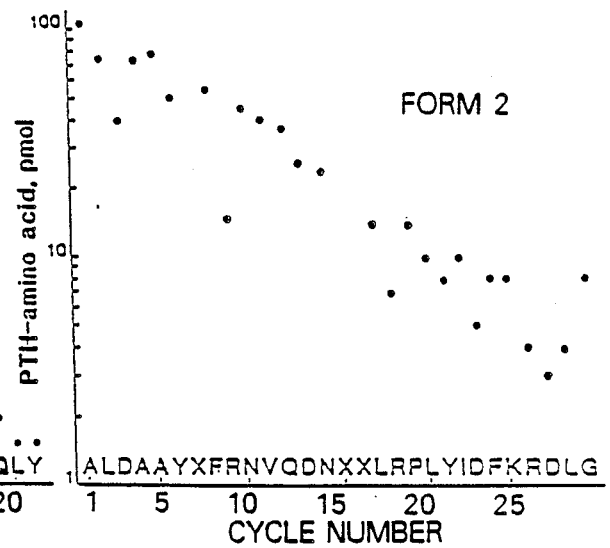
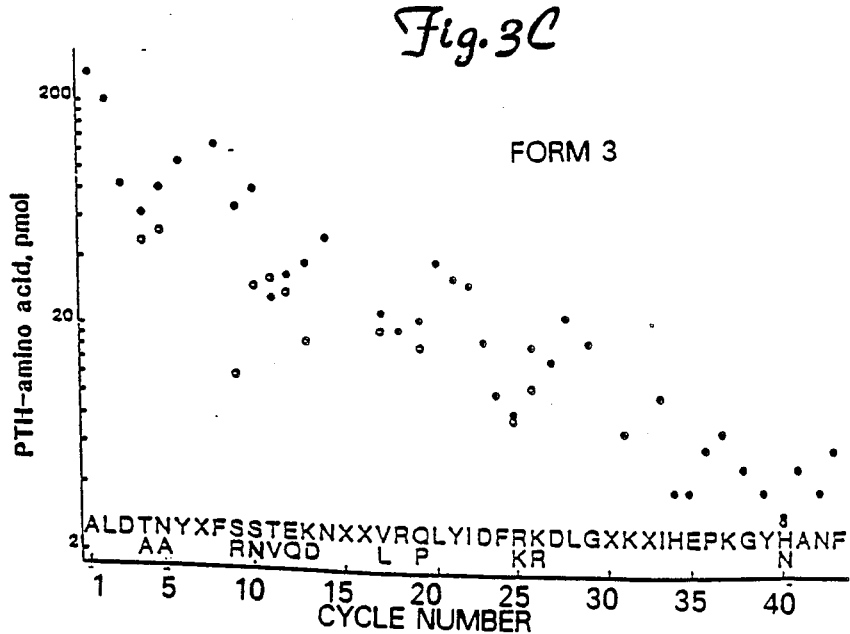

STABILIZED INTERLEUKIN-2

The invention concerns both stabilizing a preparation of interleukin-2 intended for therapeutic purposes, especially in humans and animals, and a preparation obtained accordingly in the form of aqueous solutions or solid forms.

Lymphokines, in their capacity as hormone-like signal transmitters, carry out a central function in creating and regulating immune responses (Sorg, C. and Schimpel, A., Cellular and Molecular Biology of Lymphokines, Orlando, Academic Press, 1985, and Gillis, S. and Inman, F. P., Contemporary Topics in Molecular Immunology, Vol. 10, The Interleukins, New York & London, Plenum Press, 1985). A series of immunological activities is controlled by one lumphokine, specifically interleukin-2 (IL-2). Within the overall framework of cellular immune response, interleukin-2 affects the release of other lymphokines: IFN-gamma, BCGF, and BCDF (Greene, W. C. and Robb, R. J., Receptors for T-Cell Growth Factor: Structure, Function and Expression on Normal and Neoplastic Cells, Contemporary Topics in Molecular Immunology, vol. 10, 1–34 (1985)).

Human interleukin-2 (also called TCGF) is a glycoprotein produced in small quantities by human peripheral T cells (T lymphocytes) subsequent to stimulation by antigens, mitogens (Mier, J. W. and Gallo, R. C., Purification and Some Characteristics of Human T-Cell Growth Factor from Phytohaemagglutinin-Stimulated Lymphocyte-Conditioned Media, Proc. Natl. Acad. Sci. 77, 6134–38 (1980)), or appropriate monoclonal antibodies (with the "first signal" being activation) (Cantrell, D. A. and Smith, K. A., The Interleukin-2 T-Cell System: A New Growth Model, Science 224, 4655, 1312–1316 (1984)).

Interleukin-2 provides the "second signal" in the immune response (Wagner, H., Hardt, C., Heeg, K., Pfitzenmaier, K., Solbach, W., Bartlet, R., Stockinger, H., and Röllinghof, M., In Vivo and in Vitro Effects of Interleukin-2, Immunol. Rev. 51, 215–36 (1980) and Watson, J. and Mochizuki, D., Interleukin-2: A Class of T-Cell Growth Factors, Immunol. Rev. 51, 257 (1980)) and represents a proliferation-and-regulation factor by means of which neoplastic T cells can be continuously raised in vitro. The effectiveness of interleukin-2 is evident in its in-vivo and in-vitro activation of alloreactive and tumor-reactive T cells, natural and lymphokine-activated killer-cell populations as well as helper, suppressor, and cytotoxic T cells. Human interleukin-2 also stimulates the proliferation of cells that depend on mouse or rat interleukin-2.

Human interleukin-2 (n IL-2) is a protein formed of 133 amino acids. It is hydrophobic. It is glycosylated at position 3 by the amino acid trieonine. According to its microheterogenous glycosylation pattern during post-translational modification, human interleukin-2 exhibits, as its degree of glycosylation drops, at least three molecular species at 17, 16, and 14.5 kD (SDS-Page) (Körner, I. J., Dettmer, R., Kopp, J., Gaestel, M., and Malz, W., Simple Preparative Two-Step Purification of Interleukin-2 from Culture Medium of Lectin-Stimulated Normal Human Lumphocytes, J. Immunol. Meth. 87, 185–191 (1986)).

Activated but non-resting T cells express high- and low-affinity interleukin-2 receptors (Robb, R. J., Greene, W. C., & Rusk, C. M. Low- and High-Affinity Cellular Receptors for Interleukin-2, J. Exp. Med. 160, 1126–46 (1984) and Robb, R. J., Interleukin-2 and its Cell-Surface Receptor, Behring Inst. Mitt. 77, 55–67 (1985)). A maximum number of interleukin-2 receptors will form on normal lymphocytes treated with mitogens within approximately 60 hours, with a total of approximately 20 000 per normal T cell.

The bonding of interleukin-2 in the capacity of peptide hormone to interleukin-2 receptors and its subsequent internalization, finally, triggers cell division (Robb, R. J., Interleukin-2 and its Cell-Surface Receptor, Behring Inst. Mitt. 77, 55–67 (1985)). The signals are transmitted from cell to cell at this point through a cascade of signal communications, which $Ca^{2+}$ participates in, and through downstream phosphorylation of the ribosome protein S 6 prior to translation.

The production and purification of human interleukin-2 is described in the literature (Sonneborn, H.-H. and Schwulera, U., Production, Purification, and Properties of Human Interleukin-2 (IL-2), Biotest-Bulletin 1, 3, 222–27 (1982)).

In addition to its use in the laboratory and for diagnostic purposes, interleukin-2 can also be employed therapeutically in humans and animals, to inhibit tumor growth for example. The most recent research indicates that multiple intratumoral injections in the mouse model can lead to deceleration of tumor growth to the extent of complete rejection.

A high-purity interleukin-2 preparation is a prerequisite for injection and infusion. The purer the preparation, however, the more unstable its biological activity.

However, since as previously discussed herein, only small amounts of human interleukin-2 can be obtained from human peripheral T cells, large amounts will have to be stored for a fairly long time in the form of solutions, deep-frozen batches, or lyophilizates of a high-purity interleukin-2 preparation to allow its extended and reliable clinical use as a therapeutic and especially antitumoral agent. Drug authorities for instance require that a therapeutic agent remain stable at least one year, a demand that no known preparation has satisfied as yet.

The activity of high-purity interleukin-2 in the context of therapy, however, decreases when it is stored very long, especially when deep-frozen, thawed, or lyophilized.

The object of the invention is accordingly to provide a high-purity interleukin-2 preparation that will be appropriate for therapeutic purposes, especially in humans, that will remain stable when stored for a long time, and that will continue to exhibit sufficient activity after being deep-frozen, lyophilized, and even thawed several times.

This object is attained in accordance with the invention by using a particular stabilizer as characterized hereinbelow.

It was surprisingly discovered that substances—such as globulins, sugar alcohols, monomeric and polymeric sugars, gelatins, and mixtures thereof—not yet known as stabilizers for interleukin-2, do indeed stabilize it very well. In addition to a series of other known stabilizers—such as for example SH-reducing compounds, glycerin, and polyethylene glycols, albumins, and especially human-serum albumin, are already known as stabilizers for lower-purity interleukin-2 preparations.

It is, however, completely surprising that albumins selected on the basis of a special method of characterization have the capacity to stabilize for long periods even the high-purity interleukin-2 preparations previously described herein as being especially likely to lose their activity unless stabilized. Specially characterized albumins are to be understood herein as those that exhibit the criteria that will be described hereinbelow for albumins that can be used to stabilize interleukin-2 for therapeutic purposes. It has been discovered that high-purity interleukin-2 will, when stabilized with a specially characterized human-serum albumin of this type, retain 85% of its activity when stored for 12 months at 37° C., 90% when stored that long at 22° C., and even 95% for the same period at 4° C. and will accordingly completely comply with the authorities's requirements that a therapeutic preparation remain sterile at least one year. With no stabilizer added, a high-purity interleukin-2 preparation will lose its activity in accordance with its protein concentration.

Even freeze-drying will not stabilize an interleukin-2 preparation unless a stabilizer is added.

Table I provides a comparison of the properties of interleukin-2 preparations for laboratory and for therapeutic purposes.

TABLE I

| | Laboratory preparation | Infusion preparation |
|---|---|---|
| Purpose: | in-vitro tests | in-vivo therapy |
| 0.1 μm filtering | sterile | sterile |
| Pyrogenicity (as determined from limulus and rabbit tests) | may be pyrogenic | must be pyrogen-free |
| Toxicity | should be free of cytotoxic factors | must be free of toxins, both in acute toxicology in two species and in chronic toxicology |
| Added stabilizer | should have stabilizing action (obtaining biological activity) | should have stabilizing action and be non-toxic and pharmacologically unobjectionable |
| Mitogenicity | can but must not be free of mitogens, with the preparation selected in accordance with purpose | must be free of mitogens |
| Immunogenicity | can be immunogenic (most of the r IL-2 immunogenic preparations e.g.) | must not be |
| Physiological environment (buffer, ion strength, osmolality, pH) | is supplied as a ready-to-use tissue-culture additive and is also commercially available as a concentrate | must be completely within a physiological environment |

TABLE I-continued

| Manufacture | in accordance with inherent guidelines and quality control | Good manufacturing practice in accordance with standards and maintaining the guidelines of the prevailing pharmacopoeia |
|---|---|---|

A high-purity interleukin-2 preparation that is especially appropriate for processing in accordance with the invention is one prepared by the method disclosed in German OS 3 411 184 and U.S. Pat. No. 4,508,833 (corresponding to German P 3 149 360.2).

In this method the interleukin-2 is prepared from human peripheral-blood lymphocytes by adding a phorbol ester, especially β-phorbol-12-myrisate-13 acetate (PMA) and Calcium Ionophor A 23 187 (6S-[6-α-(2S*,3S*),8β(R*),9β,11-α]-5-(methylamino)-2-[[-3,9,11-trimethyl-8-[1-methyl-2-oxo-2-(1H-pyrrol-2-yl)-ethyl]-1,7-dioxaspiro-[5.5]-undec-2-yl]-methyl]-4-benzoxazole-carboxylic acid, cf. the brochure Calbiochem-Behring, Doc. No. 8154-1082 Biologics, Antibiotica A 23187) and by employing several chromatographic purification stages. The resulting product has the following characteristics:

| | |
|---|---|
| Purity: sodium dodecylpolyacrylamide gel electrophoresis (stained silver): | >95%<br>MW 16 500-15 500: glycolized IL-2<br>MW 14 500: non-glycolized Il-2 (no other proteins were found even when the gel was overloaded) |
| Interleukin-2 activity: | at least $10^6$ U/ml (from comparison with the current IUIS reference) |
| Specific activity: | at least $10^7$ U/mg of protein |
| Pyrogens (endotoxins): | no evidence |
| Mycoplasmas: | no evidence |
| Nucleic acids: | no evidence |
| Proteases: | free of all activity |
| Foreign activity: | no evidence (tested for MIF, LIF, MF, GM-CSF, GIF, IL-1, IL-3, α-IFN, LF, MAF (MCF), and GCI) |
| Biological activity: | $^3$H—Tdr incorporation and 7-day growth of human CON-A, PHA, or MLC blasts. |

Table II lists stabilizers that are appropriate in accordance with the invention along with their stabilization effect on the previously described interleukin-2 preparations.

| Stabilizer | IL-2 concentration U/ml | Stabilizer concentration | | Activity remaining after storage 7 days at 4° C. | Freezing and thawing 5 times | Activity remaining after storage 7 days at 37° C. | Lyophilization |
|---|---|---|---|---|---|---|---|
| None (control) | $10^5$ | | | 30% | 23% | 6% | 2% |
| Oxypoly-gelatins, | $10^5$ | 0.1% | v/v | 35% | 31% | 14% | 9% |
| 5.5% (w/v) | | 1% | | 40% | 35% | 19% | 11% |
| Dextran | $10^5$ | 0.1% | w/v | 29% | 33% | 26% | 12% |
| | | 1% | | 37% | 35% | 19% | 16% |
| Hydroxyethyl starch | $10^5$ | 0.1% | v/v | 23% | 24% | 16% | 17% |
| | | 1% | | 34% | 31% | 21% | 19% |
| Immunoglobulin, | $10^5$ | 0.1% | | 70% | 57% | 43% | 21% |

-continued

| Stabilizer | IL-2 concentration U/ml | Stabilizer concentration | | Activity remaining after storage 7 days at 4° C. | Freezing and thawing 5 times | Activity remaining after storage 7 days at 37° C. | Lyophil- ization |
|---|---|---|---|---|---|---|---|
| 5% (w/v) | | 1% | v/v | 83% | 63% | 39% | 32% |
| Fetal-calf serum | $10^5$ | 0.1% | v/v | 72% | 68% | 51% | 45% |
| | | 1% | | 78% | 77% | 59% | 63% |
| Human serum (inactivated)* 30 min. @ 56° C. | $10^5$ | 0.1% | v/v | 81% | 94% | 89% | 90% |
| | | 1% | | 97% | 86% | 91% | 92% |
| Bovine-serum albumin (Fraction V) | $10^5$ | 0.1% | w/v | 96% | 94% | 93% | 97% |
| | | 1% | | 100% | 96% | 97% | 95% |
| Human-serum albumin*, 20% w/v | $10^5$ | 0.1% | v/v | 99% | 102% | 96% | 97% |
| | | 1% | | 98% | 97% | 100% | 98% |
| Ovalbumin | $10^5$ | 0.1% | w/v | 94% | 94% | 93% | 95% |
| | | 1% | | 98% | 96% | 91% | 92% |

*Selected on the basis of the following criteria.

Another essential criterion besides stabilization activity for the selection of stabilizers for a therapeutically usable interleukin-2 preparation is that they be non-toxic and pharmacologically unobjectionable.

Table II shows that plasma expanders have a stabilizing effect on interleukin-2 and that globulins have an even more powerful one. The best results, however, will be evident in conjunction with the addition of human serum selected in accordance with a special method of characterization or with the addition of selected batches of albumin. Freezing and thawing 5 times resulted in practically no decrease in activity. Furthermore, no stabilizer protein precipitates. The same is true of the lyophilized product, whereby the effect is even more drastic in that the unstabilized control exhibits a residual activity of only 2% subsequent to lyophilization. Human-serum albumin (HSA) turned out to be particularly effective. The preferred human-serum albumin is at least 96% pure, with the percentage of monomers as high as possible and the remaining dimer and polymer share as low as possible. The pH should be between 6.7 and 7.4.

An extremely important factor in selecting an appropriate human-serum albumin is that there exist batches that inhibit interleukin-2 activity. Although the cause of this effect is not yet completely understood, it is suspected that some substance of a medicinal or other nature in the donor's cells is responsible. Every batch of human-serum albumin that is to be employed as a stabilizer must accordingly be tested for inhibition of interleukin-2 activity. This is done with a $^3$H-thymidine-incorporation test as described hereinbelow with reference to the examples. One or two days of testing is enough to determine whether a batch is inhibiting or not. The terms "appropriate" and "selected" in the instant description and claims are accordingly to be understood as meaning that a batch of human-serum albumin does not inhibit interleukin-2 activity, whereas an "inappropriate" batch is one that does inhibit it.

The criteria for selecting human-serum albumin as a stabilizer for interleukin-2 that is to be used for therapeutic purposes will now be summarized.

It will not inhibit interleukin-2 activity.
It will be non-toxic to two species in vivo.
It will be sterile.
It will be pyrogen free (in the limulus test and in rabbits).
It will have an albumin level of 96-100% (with a monomer content of 97%).
It will be heat-stable for 50 hours at 57° C.
It will not react with blood-group antibodies.
It can be released for infusion.

As will be evident from the examples and from Table III, even 0.1% of a selected batch of human-serum albumin preparation will be enough to optimally stabilize 1-$10^6$ U/ml of interleukin-2. Although higher concentrations also have a satisfactory stabilizing action, they frequently lead to albumin-dictated side effects. When the concentration of interleukin-2 is higher than $10^6$ U/ml, somewhat higher concentrations of stabilizer will be needed. Tests have shown for example that approximately 0.2-1% w/v of albumin is necessary for $10^7$-$10^8$ U/ml of interleukin-2.

Table III evidences the outstanding stabilizing action of 0.1% of a selected batch of human-serum albumin over a wide range of concentrations of interleukin-2.

TABLE III

| IL-2 Concentration, U/ml | Control, without HSA | With 0.1% (w/v) of a selected batch of HSA, % |
|---|---|---|
| 10 | 0 | 81 |
| 100 | 2 | 86 |
| 1 000 | 8 | 97 |
| 10 000 | 19 | 100 |
| 100 000 | 27 | 99 |
| 1 000 000 | 44 | 98 |

The table lists the interleukin-2 activity remaining after 1 week of storage at 4° C. Human interleukin-2 was stored in RPMI in the presence of 50 μg of streptomycin sulfate per ml and 50 IU of penicillin G with and without stabilizers. The control was optimally stabilized and stored at −70° C.

Since albumins can incompletely polymerize or denature during pasteurization it is practical to add an albumin stabilizer to the preparations. ε-Aminocaprylate and N-acetyltryptophan have proved to be appropriate stabilizers for albumins. Appropriate amounts of these stabilizers range between 0.1 and 0.04 mM, with 0.08 mM preferable.

It has also turned out to be practical for certain purposes to use mixtures of the claimed stabilizers or to use them in mixtures with other known interleukin-2 stabilizers (cf. examples).

Adding either 0.1M of L-lysine, L-tryptophan, L-arginine, up to 1 mM of monovalent or bivalent salts like NaCl, CaCl$_2$, and MgCl$_2$, or $5 \times 10^{-5}$M of sequestering agents alone have only a slight effect on the stabilization of interleukin-2 (with a residual activity that is 1–5% higher). The substances, are however, effective, depending on the purpose, in stabilization mixtures. Monosaccharides (e.g. glucose, mannose, and fructose) and disaccharides (sucrose, maltose, and lactose) alone and sugar alcohols alone at a concentration of 0.1M have only a slight effect (with a residual activity that is 3–6% higher). In a stabilizing mixture, however, especially in relation to long-term storage, it is a very good idea to add them, in conjunction with freeze drying for example.

Other additives that have already been described in the literature, like SH-reducing compounds ($\beta$-mercaptoethanol or dithiotreitol) protect interleukin-2 from oxidation (at $10^{-3}$–$10^{-5}$M). Adding 10–50% v/v of glycerin considerably decreases the inactivation of interleukin-2. A definite stabilizing effect is obtained with 0.1–10% w/v of polyethylene glycols (MW 1 500–40 000).

Some examples of stabilizing mixtures and the purposes that they are especially appropriate for will now be described.

| Mixture | Purpose |
| --- | --- |
| 0.1% human-serum albumin (selected in accordance with the aforesaid criteria) 0.8 mM tryptophan 0.01 M PBS, pH 7.4 | $-20°$ C. or storage at even lower temperatures in the deep-frozen state |
| 1% inactivated human serum (selected in accordance with the aforesaid criteria) 0.01 M PBS, pH 7.4 5% glycerin | $-20°$ or storage at even lower temperatures in the deep-frozen state |
| 50% glycerin $5 \times 10^{-5}$ M -mercaptoethanol 0.1% human-serum albumin (selected in accordance with the foregoing criteria) 0.01 M PBS, pH 7.4 | liquid storage at $-20°$ C. |
| 1% (w/v) inactivated human serum (selected in accordance with the foregoing criteria) (30 min. @ 56° C.) 2 mM L-glutamine 20 mM HEPES, pH 7.4 $5 \times 10^{-5}$ M DTT RPMI 1640 | lyophilization |
| 1% (w/v) human-serum albumin (selected in accordance with the foregoing criteria) 0.01 M PBS, pH 7.4 0.8 mM L-tryptophan 0.01 M glucose | lyophilization |
| 1% (w/v) human-serum albumin (selected in accordance with the foregoing criteria) 0.01 M PBS pH 7.4 0.8 mM L-tryptophan 0.01 M glucose | lyophilization |

Buffer systems consisting of
Tris-HCl
Na$^+$ phosphate buffer
K$^+$ phosphate buffer
Na$^{30}$—K$^+$ phosphate buffer
were also tested for their suitability as stabilizers.

All three of these buffer systems were appropriate in concentrations of 0.1–50 mM. The Na$^+$ phosphate buffer at a concentration of 10 mM was preferred because it resulted in a pH that was not too far away from that of the physiological environment.

The optimal conditions for a high-purity stabilized interleukin-2 preparation were found to be Interleukin-2 concentration: 1–10$^9$ U/ml
Buffer: 10 mM of Na$^+$ phosphate
NaCl concentration: 0.15M
Osmolarity: 287 m osmol
HSA level in selected batch: 0.1–0.2% (w/v).

The invention will be further described in the following illustrative examples in conjunction with the appended drawings wherein

BRIEF DESCRIPTION OF DRAWINGS

FIGS. 1 to 4 are plots showing the results of the respective examples.

EXAMPLE 1

The stabilizing effect of various albumin preparations on interleukin-2

The following albumin preparations were tested for their stabilizing action on interleukin-2:

inactivated human serum (HS) containing 70% human-serum albumin, inactivated fetal-calf serum (FCS) containing 70% bovine-serum albumin, Batch I: a 96% pure human-serum albumin, whereof 75% was monomer, plus an albumin stabilizer in the form of 0.08 mM of $\epsilon$-aminocaprylate and 0.08 mM of N-acetyltryptophan, and Batch II: a pure human-serum albumin from another donor.

1000 U/ml of human interleukin-2 obtained from peripheral-blood lymphocytes by the method disclosed in German OS 3 411 184 were incubated in RPMI 1640 for 1 to 3 days in a CO$_2$ incubator (5% CO$_2$ and more than 95% humidity) at 37° C. with 50 JU of penicillin G/ml, 50 mg of streptomycin sulfate/ml, and one of the aforesaid albumin preparations (HS and FCS 20%, both batches HSA 10%). This was followed by a $^3$H-thymidine-incorporation test as described in the brochure "Lumphocult" (Biotest, September 1985) with ConA-blast cells as targets. The control was the current IUIS reference standard (Lymphokine Research 3, 277 [1984]), the value of which is represented by 100% in the figures. The degree of $^3$H-thymidine incorporation is considered the indication of interleukin-2 activity.

Figure 1:
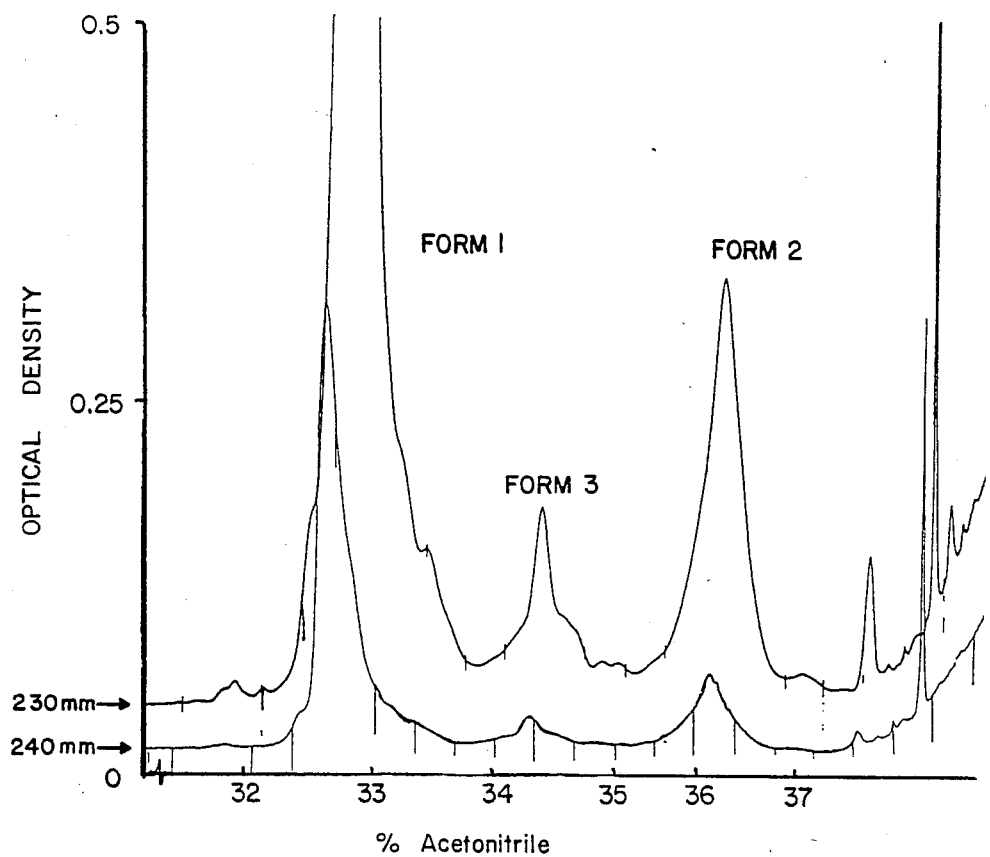

FIG. 1 illustrates the results of this test. As will be evident from the figure, the stabilizing action of both the human albumin and the fetal-calf serum was practically identical, still almost 100% after 3 days, whereas Batch I of the human-serum albumin exhibited a slight deviation, although still 100% after 3 days.

Batch II of the human-serum albumin turned out to be inappropriate. As will be evident from FIG. 2, whether a human-serum albumin batch is appropriate or not can be determined after 1 to 2 days, and definitely after 3 days.

EXAMPLE 2

Testing albumin batches for inhibition in an interleukin-2 test and determining the optimal albumin concentration of an appropriate batch 100 000 U/ml of the interleukin-2 described with reference to Example 1 plus various amounts of human-serum albumin from the two batches described with reference to Example 1 were incubated in 0.01M of PBS (phosphate buffer 0.01M with 0.15M of NaCl) for 24 hours in a $CO_2$ incubator (5% $CO_2$, more than 95% humidity) at 37° C. and a pH of 7.4. The interleukin-2 activity was then determined as described with reference to Example 1.

Figure 2:
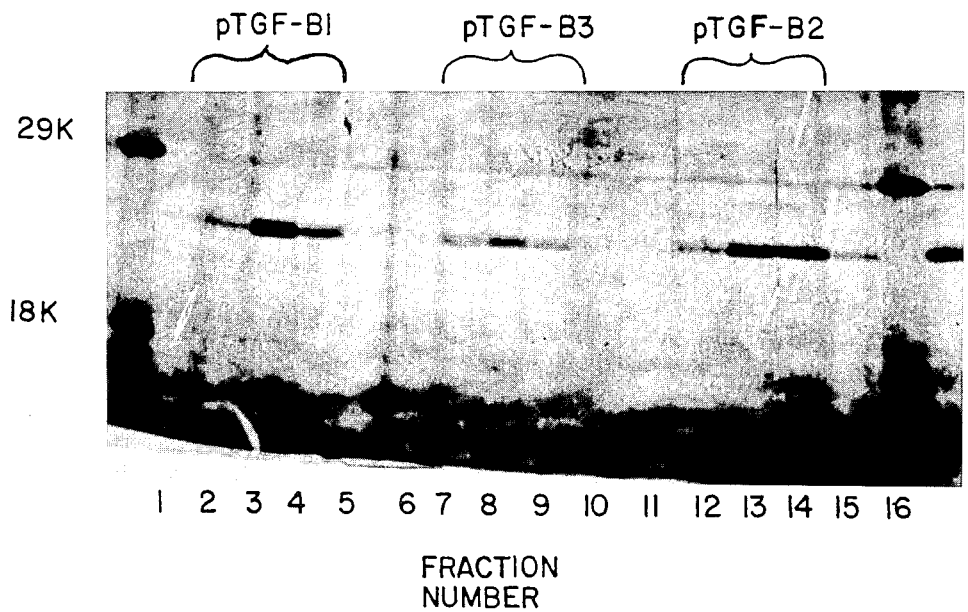

FIG. 2 shows the results.

If, as will be evident from the figure, the charge is appropriate, even 0.1% of albumin will be enough to stabilize up to $10^6$ U of interleukin-2/ml 100% optimally, whereas, if the charge is inappropriate, the inhibiting action increases with increasing albumin concentration.

EXAMPLE 3

Testing pH dependence 100 000 U/ml of the interleukin-2 from Example 1 were incubated in 0.01M of PBS with 0.1% of human-serum albumin like that in Batch I from Example 1 but without the caprylate and tryptophan in a $CO_2$ incubator (5% $CO_2$, more than 95% humidity) for 24 hours at 37° C. and a pH of 7.4. The pH was then adjusted to various values and the activity of the interleukin-2 determined as described with reference to Example 1 after 1 day of storage at 4° C.

FIG. 3 shows the results of this test.

As will be evident from the figure, the stabilized interleukin-2 was very extensively independent of pH. Only in the alkaline range was there a slight decrease in activity.

EXAMPLE 4

Figure 4A:
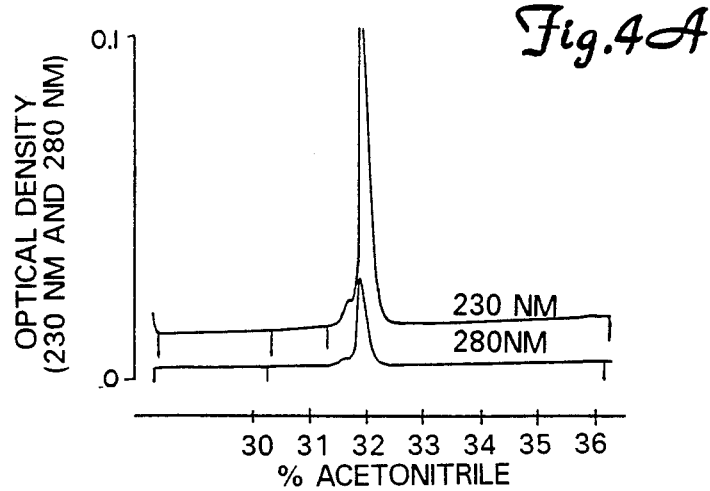
Figure 4B:
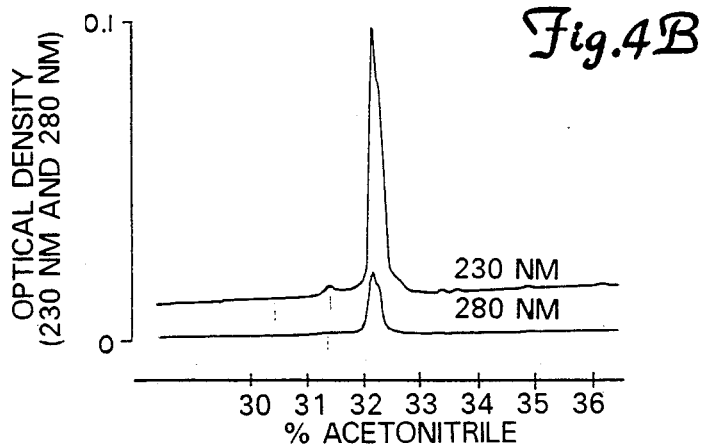
Figure 4C:
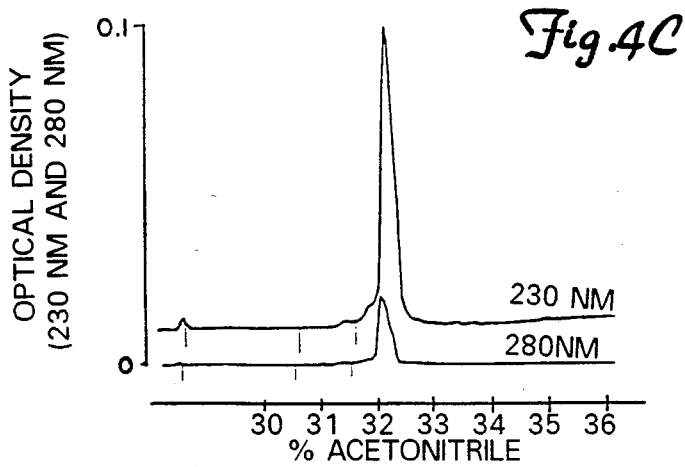

Long-term storage tests at the optimal albumin concentration at different temperatures 100 000 U/ml of the interleukin-2 from Example 1 in enough PBS to allow adjusting the pH to 7.4 and 0.1% human-serum albumin with the same characteristics as Batch I of Example 1 were stored for 12 months at the temperatures listed in FIG. 4. The activity was then determined as described with reference to Example 1.

FIG. 4 shows the results of this test.

As will be evident from the figure, it was surprisingly discovered that, in comparison to control stored at −70° C., in heat-sealed sterile ampules or in the form of a lyophilizate plus an appropriate batch of human-serum albumin, no decrease in activity was found at 4° C., although a decrease of about 10% was observable after 1 year at 22° C., which is, however, still within the margin of error for the interleukin-2 test, and that even with storage for 1 year at 37° C. only about a 15% loss in activity could be discovered. At −70° C., −20° C. and +4° C. even after 2 years no loss in activity could be discovered.

No cloudiness or precipitation was discovered in the liquid inside any of the ampules.

It is possible to employ PHA blasts or MLC blasts instead of ConA blasts in the $^3H$ thymidine-incorporation test in the foregoing research with practically the same results.

It will be understood that the specification and examples are illustrative but not limitative of the present invention and that other embodiments within the spirit and scope of the invention will suggest themselves to those skilled in the art.

What is claimed is:

1. A stabilized composition comprising interleukin-2 and a stabilizing effective amount of globulin.

2. A composition according to claim 1, further containing hydroxyethyl starch or dextran.

3. A composition according to claim 1, wherein the interleukin-2 is obtained from human peripheral-blood lumphocytes by adding mitogens or phorbol ester and calcium ionophore to the cell suspension and by chromatographic purification and has the following characteristics: purity greater than 95%, glycosylate interleukin-2 MW 16 500 to MW 15 500, non-glycosylated interleukin-2 MW 14 500, interleukin-2 activity higher than $10^2$ U/ml as compared with the provisional IUS reference, specific activity higher than $10^7$ U/mg of protein, pyrogen-free, protease-free, free of toxins, and free of other biologic activities.

4. A method for long-time stabilization of one of a natural interleukin-2-preparation obtained from lymphocytes or cell-lines and a recombinant interleukin-2, destined for therapeuticic use in humans and animals comprising adding thereto globulin and mixtures thereof with at least one of sugar alcohol, monomeric or polymeric sugar and gelatin.

* * * * *

UNITED STATES PATENT AND TRADEMARK OFFICE
CERTIFICATE OF CORRECTION

PATENT NO. : 4,904,467

DATED : February 27, 1990

INVENTOR(S) : Udo Schwulera

It is certified that error appears in the above-identified patent and that said Letters Patent is hereby corrected as shown below:

Col. 10, claim 3 line 38    Delete " $10^2$ " and substitute -- $10^6$ --, delete " IUS " and substitute -- IUIS --

Signed and Sealed this

Ninth Day of June, 1992

Attest:

DOUGLAS B. COMER

Attesting Officer

Acting Commissioner of Patents and Trademarks